(12) United States Patent
Narayanan et al.

(10) Patent No.: US 11,903,734 B2
(45) Date of Patent: Feb. 20, 2024

(54) WEARABLE MULTIPLATFORM SENSOR

(71) Applicant: International Business Machines Corporation, Armonk, NY (US)

(72) Inventors: Rajeev Narayanan, Briarcliff Manor, NY (US); Katsuyuki Sakuma, Fishkill, NY (US); John Knickerbocker, Monroe, NY (US); Bucknell C. Webb, Ossining, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 384 days.

(21) Appl. No.: 16/238,143

(22) Filed: Jan. 2, 2019

(65) Prior Publication Data
US 2020/0205735 A1 Jul. 2, 2020

(51) Int. Cl.
*A61B 5/00* (2006.01)
*G06F 3/01* (2006.01)
*H02S 40/30* (2014.01)

(52) U.S. Cl.
CPC .......... *A61B 5/6826* (2013.01); *A61B 5/6833* (2013.01); *G06F 3/015* (2013.01); *H02S 40/30* (2014.12)

(58) Field of Classification Search
None
See application file for complete search history.

(56) References Cited

U.S. PATENT DOCUMENTS

| 5,293,879 | A | | 3/1994 | Vonk et al. |
| 6,018,673 | A | * | 1/2000 | Chin ................. A61B 5/14552 356/41 |
| 6,181,329 | B1 | | 1/2001 | Stork et al. |
| 6,897,854 | B2 | | 5/2005 | Cho et al. |
| 7,508,384 | B2 | | 3/2009 | Zhang et al. |

(Continued)

FOREIGN PATENT DOCUMENTS

| CN | 104127187 A | 11/2014 |
| CN | 104127187 B | 4/2017 |
| WO | 2017037487 A1 | 3/2017 |

OTHER PUBLICATIONS

Reinertsen et al., "A review of physiological and behavioral monitoring with digital sensors for neuropsychiatric illnesses," 2018, Institute of Physics and Engineering in Medicine, Physiological Measurement, vol. 39, No. 5, pp. 1-38 (Year: 2018).*

(Continued)

*Primary Examiner* — Alex M Valvis
*Assistant Examiner* — Aurelie H Tu
(74) *Attorney, Agent, or Firm* — Amin, Turocy & Watson, LLP

(57) ABSTRACT

Systems, computer-implemented methods and/or computer program products that facilitate wearable multiplatform sensing are provided. In one embodiment, a computer-implemented method comprises: measuring, by a system operatively coupled to a processor, wirelessly on a nail plate, physiological data of an entity; integrating and synchronizing, by the system, the physiological data with other physiological data from one or more devices to form integrated physiological data; and analyzing, by the system, the integrated physiological data to detect one or more disorders.

20 Claims, 13 Drawing Sheets

(56) References Cited

U.S. PATENT DOCUMENTS

| | | | |
|---|---|---|---|
| 7,730,547 B2 | 6/2010 | Barrera et al. | |
| 2005/0103114 A1* | 5/2005 | Bly | G01L 9/0042 |
| | | | 73/754 |
| 2008/0058622 A1* | 3/2008 | Baker | A61B 5/14552 |
| | | | 600/344 |
| 2010/0106060 A1* | 4/2010 | Tsuji | A61B 5/225 |
| | | | 600/587 |
| 2012/0083700 A1* | 4/2012 | Osorio | A61B 5/11 |
| | | | 600/483 |
| 2013/0123666 A1* | 5/2013 | Giuffrida | A61B 5/0022 |
| | | | 600/595 |
| 2014/0134575 A1* | 5/2014 | Kim | G09B 21/025 |
| | | | 434/114 |
| 2014/0155718 A1* | 6/2014 | Kramer | A61B 5/449 |
| | | | 600/344 |
| 2014/0155784 A1* | 6/2014 | Smith | G06K 9/6229 |
| | | | 600/595 |
| 2016/0313798 A1* | 10/2016 | Connor | A61B 5/0059 |
| 2017/0164876 A1* | 6/2017 | Hyde | A61B 5/4836 |
| 2018/0085061 A1* | 3/2018 | Heisig | G01B 7/20 |
| 2018/0279940 A1* | 10/2018 | Campbell | A61B 5/0059 |
| 2018/0317789 A1* | 11/2018 | Ransbury | A61B 7/04 |
| 2018/0353152 A1* | 12/2018 | Teji | A61B 7/003 |
| 2020/0121204 A1* | 4/2020 | Sakuma | A61B 5/1072 |

OTHER PUBLICATIONS

Sakuma, Katsuyuki, et al., Wearable Nail Deformation Sensing for Behavioral and Biomechanical Monitoring and Human-Computer Interaction, Dec. 2018, Scientific Reports, vol. 8, pp. 1-11 (Year: 2018).* hitachi.com, "Hitachi Announces to Begin Volume Production of Semiconductor Strain Sensors for IoT," News Release Jul. 3, 2015, 3 pages.

Parsons, et al., "A controlled clinical comparison of attention performance in children with ADHD in a virtual reality classroom compared to standard neuropsychological methods," Child Neuropsychol. Jul. 2007;13(4), Abstract, 1 page.

Ayyildiz, et al., "An Optoelectromechanical Tactile Sensor for Detection of Breast Lumps," IEEE Transactions on Haptics, vol. 6, No. 2, Apr.-Jun. 2013, 11 pages.

Perez, et al., "A wearable interface that helps the diagnosis of ADHD behavior based on biofeedback technology," Last Accessed: Nov. 13, 2018, 7 pages.

pressureprofile.com, "Revolutionizing Cancer Detection with Capacitive Tactile Sensing," Retrieved: Oct. 25, 2018, 4 pages.

Parsons, et al., "Virtual Reality Stroop Task for neurocognitive assessment," Stud Health Technol Inform. 2011;163, Abstract, 1 page.

Mel, et al., "The NIST Definition of Cloud Computing," NIST Special Publication 800-145, Sep. 2011, 7 pages.

* cited by examiner

WEARABLE MULTIPLATFORM SENSOR

BACKGROUND

The subject disclosure relates to wearable multiplatform sensor, and more specifically, facilitating wearable multiplatform sensing.

SUMMARY

The following presents a summary to provide a basic understanding of one or more embodiments of the invention. This summary is not intended to identify key or critical elements or delineate any scope of the particular embodiments or any scope of the claims. Its sole purpose is to present concepts in a simplified form as a prelude to the more detailed description that is presented later. In one or more embodiments described herein, systems, computer-implemented methods, apparatus and/or computer program products that facilitate wearable multiplatform sensing are provided.

According to one embodiment, a system is provided. The system can comprise a memory that stores computer executable components. The system can also comprise a processor, operably coupled to the memory, and that can execute computer executable components stored in the memory. The computer executable components can comprise one or more sensors that measure physiological data of an entity, wherein the one or more sensors are wireless wearables on a nail plate. The computer executable components can further comprise an integration component that integrates and synchronizes the physiological data with other physiological data from one or more devices to form integrated physiological data. The computer executable components can further comprise a data processing component that analyzes the integrated physiological data to detect one or more disorders.

According to another embodiment, a computer-implemented method is provided. The computer-implemented method can comprise measuring, by a system operatively coupled to a processor, wirelessly on a nail plate, physiological data of an entity. The computer-implemented method can further comprise integrating and synchronizing, by the system, the physiological data with other physiological data from one or more devices to form integrated physiological data. The computer-implemented method can further comprise analyzing, by the system, the integrated physiological data to detect one or more disorders.

According to another embodiment, a computer program product for facilitating wearable multiplatform sensing is provided. The computer program product can comprise a computer readable storage medium having program instructions embodied therewith. The program instructions can be executable by a processor to cause the processor to measure, by the processor, wirelessly on a nail plate, physiological data of an entity. The program instructions can further be executable by a processor to cause the processor to integrate and synchronize, by the processor, the physiological data with other physiological data from one or more devices to form integrated physiological data. The program instructions can further be executable by a processor to cause the processor to analyze, by the processor, the integrated physiological data to detect one or more disorders.

DETAILED DESCRIPTION

Figure 1:
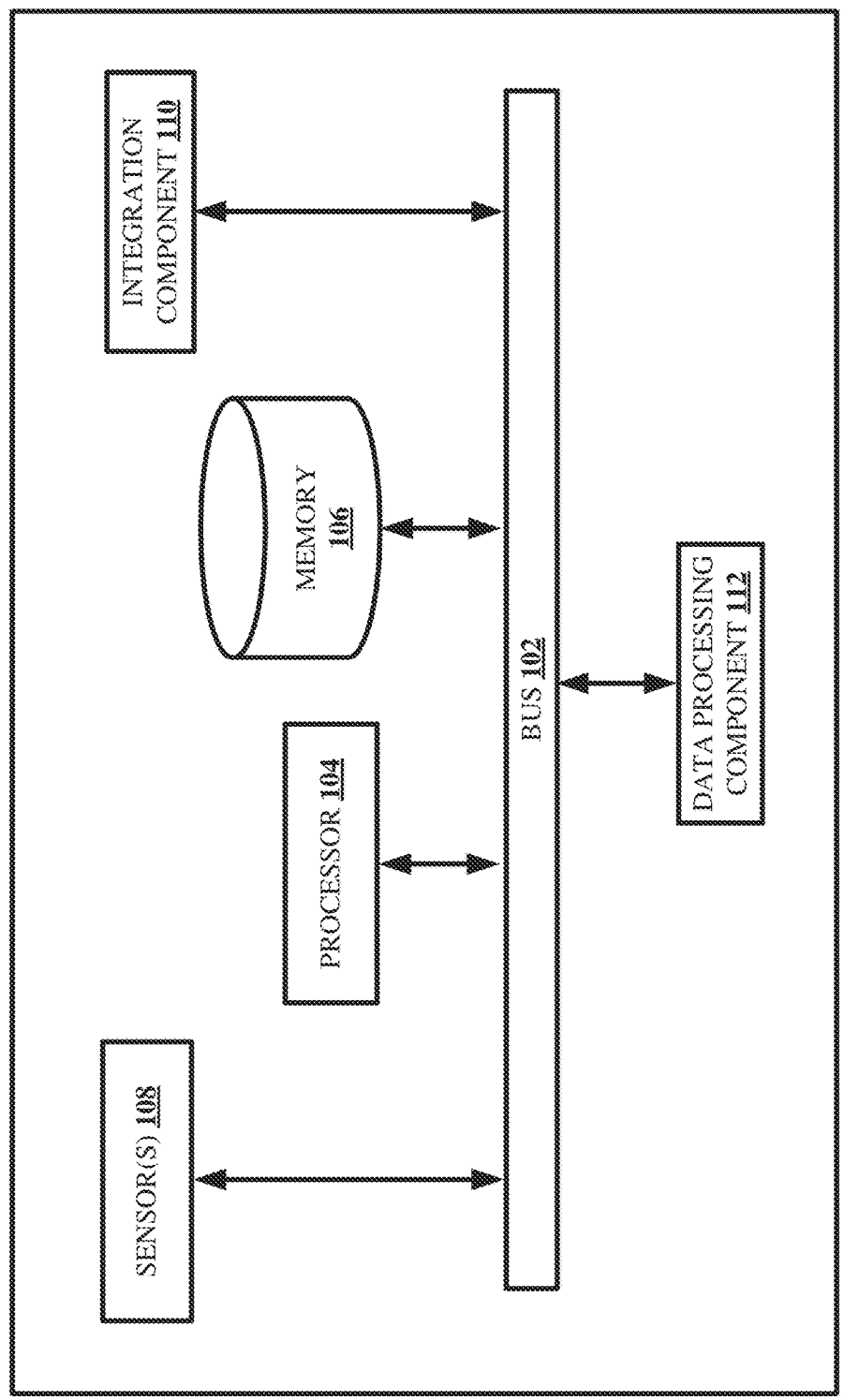
FIG. 1 illustrates a block diagram of an example, non-limiting system facilitating wearable multiplatform sensing in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

One or more embodiments described herein relates to an integrated sensor platform such as, but not limited to, electroencephalogram (EEG), electrocardiography (ECG), electromyography (EMG), strain gauge, contact lens, accelerometer, proximity, gyroscope, etc., can assist in providing data for neurological disorder and understanding of tremor and gestures as part of everyday living. Neurological sensors can provide healthcare providers and patients with valuable insights for wellness, tracking, preventive medicines and quality of life improvements. Individual microsystem unit (e.g., microsystem, sensor system, system, device, microsensor device, sensor device, etc.) can be very small and low-cost and can be attached to the nail plate, fingernail and/or toenail (e.g., generally, fingernail) for several weeks or months.

The fingernail and/or toenail sensors (e.g., generally, fingernail sensors) can be used in conjunction with other physiological sensors such as, but not limited to, EEG, ECG and EMG to assess the cognitive state of patients suffering from neurological diseases. Physiological sensors can be used to study medication on/off states and disease progression in patients. Data from fingernail sensors and smart contact lenses can be used to make quantitative measurements in neurophysiological assessment of patients. Fingernail sensors can also be used in palpation exams or other self-exams for early cancer detection.

Ultimately, the data from the multiple sensors can correlate a person's activity level. The resulting data can be extremely useful for targeted medicine, virtual writing and controls. A wearable integrated sensor environment for virtual writing without need for a writing platform. The device can capture finger movements and gestures and can be used as a freelance writing apparatus on any surface or no surface at all. Individual wearable microsystem unit can be very small, for example, 8 millimeter (mm) by 8 mm by 5 mm, and low-cost and can be attached to the fingernail for several weeks or months. This device can be used for a wide range of applications such as signature, markers, security, gestures, patient monitoring, tracking activities of daily living, human to computer or machine interface and applications beyond human use such as robotics with controlled loop feedback or other applications. A system can be programmed separately from another system. A thin metal coating on the overall package can provide moisture barrier. The device can be used as a biocompatible, ecofriendly, implantable device on animals or humans to measure weight, temperature, pressure points, etc.

Elements of hardware or structures of the microsystem can comprise a combination of strain gauge; sensors such as accelerometers, gyroscopes, proximity sensors, motion sensors, smart contact lens, etc.; temperature sensors; and/or light emitting diodes (LEDs) or light sensors such as photoplethysmography (PPG) sensors; energy harvesting cells; EEG; ECG; EMG; respiration rate monitors; sound sensors; global positioning systems (GPSs); light or darkness sensors or indicators. Integrated microsystem can comprise electronic components such as, but not limited to, microcontroller; nonvolatile memory; secure or encrypted communication components for sending and receiving data; power source components for energy efficiency such as powering of sensors on or off between use, internal and/or external energy source such as, but not limited to batteries, capacitors, supercapacitors, near field communication (NFC) power transfer, energy scavenging (e.g., energy harvesting, power harvesting or ambient power), one-time use or rechargeable battery or flexible battery; antenna; sealing barrier packaging or hermetic sealing such as, but not limited to, polymer, metal or polymer structure surrounding electronics for prolonged use, life and reliability. Electrical feedthrough for sensor elements can be used with the hermetic or sealed barrier. Antenna or other functional hardware elements can be outside the hermetic or sealed barrier.

Microsystems can be less than 500 µm to 1000 µm thick and less than 4 to 8 mm in the X and Y dimensions or 5 to 10 mm in diameter. Larger systems can also be possible. An adhesive can be used to mount the microsensor device or microsystem to the targeted location. An example adhesive can be, but not limited to, an acrylate and/or acrylic adhesive such as cyanoacrylate glue, a two-sided flexible adhesive tape or film that can permit the device to be applied to a fingernail or toenail or another location, remain during use and be removed from the user (e.g., person, human, animal, robot or entity) when completed. Adhesives can be removed from the sensor systems, and the sensor systems can be sterilized if necessary for reuse or be disposed. Alternate adhesives can be, but not limited to, biocompatible glue or film that can be applied for attachment to desired location and removed by using a solvent, stretching or peeling the sensor from the application location on the user. Multi-sensor systems can be applied to different locations that can complement data collected from other multi-sensor systems. For example, sensors on fingernails can provide information related to activities of everyday life such as eating, bathing, clothing, opening doors, picking up a cup of coffee, etc., while sensors located on toenails or other locations on a user, on or inside an animal, on a robot, etc., can collect other types of data.

Smart multiplexing can enable data streams between sensors in a system. Algorithms and timing or coordination can be employed in multiplexing data streams in order to provide value to the user application. For example, multiplexing accelerometer sensor data with the strain gauge sensor data can provide insights on grip strength, grip pressure and force applied by a user. The algorithmic outcome of such an analysis can be important for a person undergoing physiotherapy or athletes during strength training. Multiplexing can include sensor device or partial sensor device synchronization. Sensor devices can be coordinated with other sensor devices from other suppliers or on other users in a room, building or at a different location.

Additional examples of hardware elements can also include, but not limited to, sound sensors, display sensors, vibration sensors, smell sensors, alarm sensors or other communication devices. Positioning and orientation of the sensors within a device and location of the device on the user can be optimized using machine learning to support user application. Example location can be, but not limited to, near the center of the fingernail, which can provide large data or signal relative to background sensing data. For other applications, location can be optimized for sensor attachment or implant.

One or more readers or base stations can track user information and share between devices, base stations, readers or cloud. A reader or base station can comprise wireless power transfer antenna; electronics to support power transfer; data communications; communication to one or more microsystems; clocking; data logging; recording and transferring to smart phone, cloud or other secure or encrypted systems; local or mobile power supply; smart phone or smart device or multiple readers; and smart systems coordinating data from the multiple systems for algorithm analysis, etc. Locations of the base station can be in a house, car, train, plane, automobile, bicycle, robot, bed, at work, etc. Access to the base station can be by authorized individual, caregiver, doctor, family member, etc.

The subject disclosure is directed to computer processing systems, computer-implemented methods, apparatus and/or computer program products that facilitate efficiently and automatically (e.g., without direct human involvement) wearable multiplatform sensing. Humans are also unable to perform the embodiments described herein as they include, and are not limited to, performing, e.g., complex Markov processes, Bayesian analysis, or other artificial intelligence-based techniques based on probabilistic analyses and evaluating electronic information indicative of integrated physiological data, and/or determining whether countless multitudes of probability values assigned to integrated physiological data exceed or fall below various defined probability values.

The computer processing systems, computer-implemented methods, apparatus and/or computer program products employ hardware and/or software to solve problems that are highly technical in nature. For example, problems are related to automated processing, determining or inferring integrated physiological data. These problems are not abstract and cannot be performed as a set of mental acts by a human. For example, a human, or even thousands of humans, cannot efficiently, accurately and effectively manually apply countless or thousands of data and perform analysis to determine integrated physiological data.

To aid in the numerous inferences described herein (e.g., inferring integrated physiological data), components described herein can examine the entirety or a subset of data to which it is granted access and can provide for reasoning about or inferring states of a system, environment, etc., from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data.

Such inference can result in construction of new events or actions from a set of observed events and/or stored event data, whether the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x3, x4, xn), to a confidence that the input belongs to a class, as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

FIG. 1 illustrates a block diagram of an example, non-limiting system 100 facilitating wearable multiplatform sensing in accordance with one or more embodiments described herein. Aspects of systems (e.g., non-limiting system 100 and the like), apparatuses or processes explained in this disclosure can constitute machine-executable components embodied within machines, e.g., embodied in one or more computer readable mediums (or media) associated with one or more machines. Such components, when executed by the one or more machines, e.g., computers, computing devices, virtual machines, etc., can cause the machines to perform the operations described.

In various embodiments, the system 100 can be any type of component, machine, device, facility, apparatus, and/or instrument that comprises a processor. In some embodiments, the system 100 is capable of effective and/or operative communication with a wired and/or wireless network. Components, machines, apparatuses, devices, facilities, and/or instrumentalities that can comprise the system 100 can include, but are not limited to, tablet computing devices, handheld devices, server class computing machines and/or databases, laptop computers, notebook computers, desktop computers, cell phones, smart phones, consumer appliances and/or instrumentation, industrial and/or commercial devices, digital assistants, multimedia Internet enabled phones, multimedia players, and the like.

As illustrated in FIG. 1, the system 100 can comprise a bus 102, processor 104, memory 106, one or more sensors 108 (as used herein, sensors 108), integration component 110 and/or data processing component 112. The bus 102 can provide for interconnection of various components of the system 100. The processor 104 and memory 106 can carry out computation and/or storage operations of the system 100 as described herein. It is to be appreciated that in some embodiments one or more system components can communicate wirelessly with other components, through a direct wired connection or integrated on a chipset.

The system 100 can be a system-on-chip (SoC) or system-on-package (SoP) comprising one or more sensors 108. In various embodiments, the sensors 108 can measure physiological data of an entity. The sensor 108 can be a temperature sensor to measure temperature changes. The sensors 108 can comprise strain gauge sensors. The sensors 108 can be placed at locations that can be used to measure low and high frequency vibrations, pressure change (e.g., force), weight measurements and so forth. The strain gauge sensors can be semiconductor strain gauge die having a thickness less than 100 micrometer (μm) or metal strain gauge. The strain gauge sensors can be located on or embedded in flexible organic substrate material. The strain gauge sensors can be attached on first side or a second of the flexible organic substrate material, wherein the first side is opposite the second side and wherein the first side is disposed on a surface of a body of the entity. The first side can be the side on the flexible organic substrate that is attached with strain gauge sensors. If the strain gauge sensors are embedded in the flexible organic substrate, the side of the flexible substrate that is attached to a body of an entity or user can be the side that is closer to the strain gauge sensors from the surface of the sensor device. See FIG. 9 example E4 for further illustration.

The sensors 108 can be fingernail sensors and/or toenail sensors. The sensors 108 can be used in conjunction with other physiological sensors like EEG to assess the cognitive state of patients suffering from neurological disease. The sensors can also be used to study medication on/off states and disease progression in these patients. Other physiological sensors can also be smart contact lenses. Data from fingernail sensors (e.g., system 100, device comprising sensor 108, etc.) and smart contact lenses (e.g., other physiological sensors or devices) can be used to make quantitative measurements in neurophysiological assessment of patients. Fingernail sensors can be used in palpation exams or other exams for early disease detection by medical practitioners or patients for self-exams. Fingernail sensors can be radiation-free and pain-free. Fingernail sensors can comprise strain gauge sensors and attached to the fingers. The sensors 108 can comprise a flexible pressure sensing pad that can capture pressure distribution between two objects in direct physical contact to detect tumors or cancer. Fingernail sensors can also capture finger movements/gestures and can also be used as a freelance writing apparatus on surfaces or no surface.

During complementary metal oxide semiconductor (CMOS) or sensor fabrication process, sensor elements such as control circuits, amplifier circuits and analog-to-digital (A/D) converter can be constructed in a single chip. The strain gauge sensors (e.g., sensors 108) can use a modular form so that the strain gauge sensors can be modified or replaced with other sensors to measure a broad range of physical changes, including, but not limited to, weight, pressure, torque, tension, shear force and low frequency vibrations.

The fingernail sensors can be used for neuropsychological testing. Neuropsychological testing can comprise monitoring finger movements such as fidgeting, gaze and head movement among other parameters. Fingernail sensors can be used for finger movement tracking and smart contact lenses for gaze tracking to provide quantifiable assessment in neuropsychological testing. The strain gauge sensors can be applied to study, tremors such as in patients with Parkinson disease. The sensors 108 can be fingernail sensors that can be used to measure figure movements including, but not limited to, fidgeting in attention deficit hyperactivity disorder (ADHD) patients and smart contact lenses that can be used for eye tracking.

The integration component 110 can integrate and synchronize the physiological data with other physiological data from one or more devices to form integrated physiological data. The system 100 can be a primary (e.g., primary device) and the other one or more devices can be a secondary (e.g., secondary device). For example, the system 100 can be a primary device that can request data from one or more secondary devices. The primary system 100 can control operation of the secondary devices. The overall system 100 can work in a primary-secondary protocol. At any given time, there can be one primary device with one or more secondary devices. Any sensor system (e.g., system 100 or the like) can be a primary device based on a user's application that can be configured. For example, a fingernail sensor can be a primary device while other sensor system (ECG, EMG, EEG, contact lens) can be secondary devices.

The integration component 110 can integrate physiological data collected from multiple wearable sensor devices. The integration component 110 can integrate sensor devices including, but not limited to, EEG, strain gauge, smart contact lens, accelerometer, proximity sensors, gyroscope, motion sensor, temperature sensor, LED or light sensors such as PPG, EMG, respiration rate monitor, sound sensor, GPS and light or darkness sensor or indicator. The data integrated from the sensors 108 and other sensor devices (e.g., integrated data) can provide data for understanding neurological disorder, tremor and gestures as part of everyday living. The integrated data from multiple sensor devices can correlate a person's activity level. Smart multiplexing can be used to enable data streams from one or more sensors 108 or sensor devices (e.g., system 100), which can include complete or partial sensor device synchronization. For example, physiological data from sensors 108 can be integrated and synchronized with physiological data from other devices located on a user, different users, animals or robots.

The data processing component 112 can analyze the integrated physiological data to detect one or more disorders. Integrated physiological data can be used to understand neurological disorder and understand tremor and gestures as part of everyday living. Neurological sensors can provide healthcare providers and patients with valuable insights on wellness, tracking, preventative medicines and quality of life improvements. For example, the data processing component 112 can use a data analytic algorithm to analyze the data to determine grip strength, muscle strength, grip orientation, grip rate, pressure points and so forth. In another example, fingernail sensors and smart contact lens can be used to make quantitative measurements in neuropsychological testing of patients. Fingernail sensors can also be used in palpation exams for detection of cancer. The sensors 108 can include flexible pressure sensing pad that can capture pressure distribution between two objects in direct physical contact. Analysis of pressure distribution can be used for detection of cancer, tumors, etc. In another example, analysis of tremors can be used to study Parkinson disease in patients.

Figure 2:
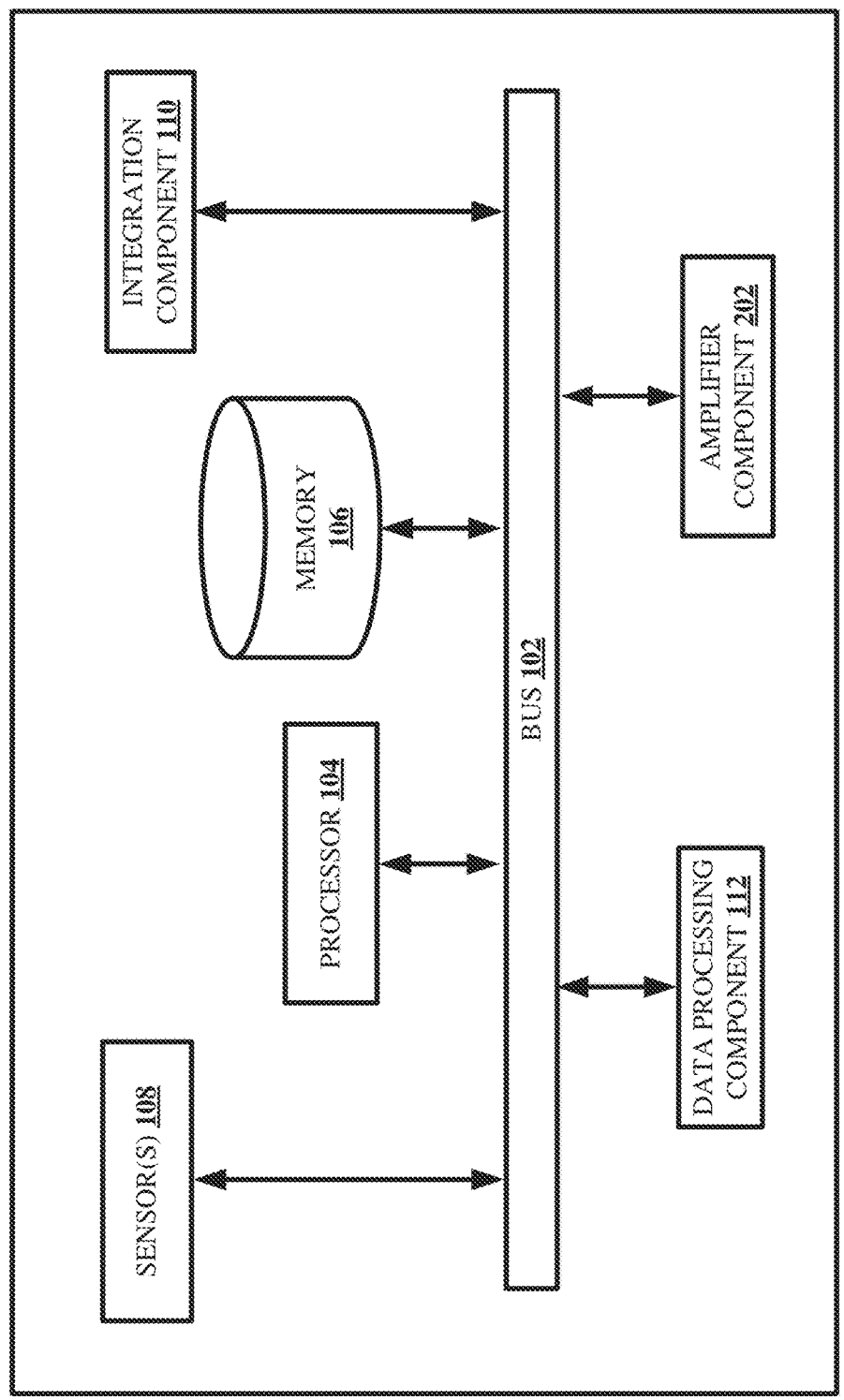
FIG. 2 illustrates a block diagram of an example, non-limiting system facilitating wearable multiplatform sensing including an amplifier component in accordance with one or more embodiments described herein.

FIG. 2 illustrates a block diagram of an example, non-limiting system facilitating wearable multiplatform sensing including an amplifier component 202 in accordance with one or more embodiments described herein. Repetitive description of like elements employed in other embodiments described herein is omitted for sake of brevity. The amplifier component 202 can amplify the physiological data from the one or more sensors. The amplifier component 202 can comprise a bridge circuit, an amplifier circuit and an A/D converter. The bridge circuit can output voltage signals upon receiving data from the sensors 108. The amplifier circuit can amplify the voltage signal output by the bridge circuit to generate an amplified signal. The A/D converter can convert the amplified signal into a digital signal.

Figure 3:
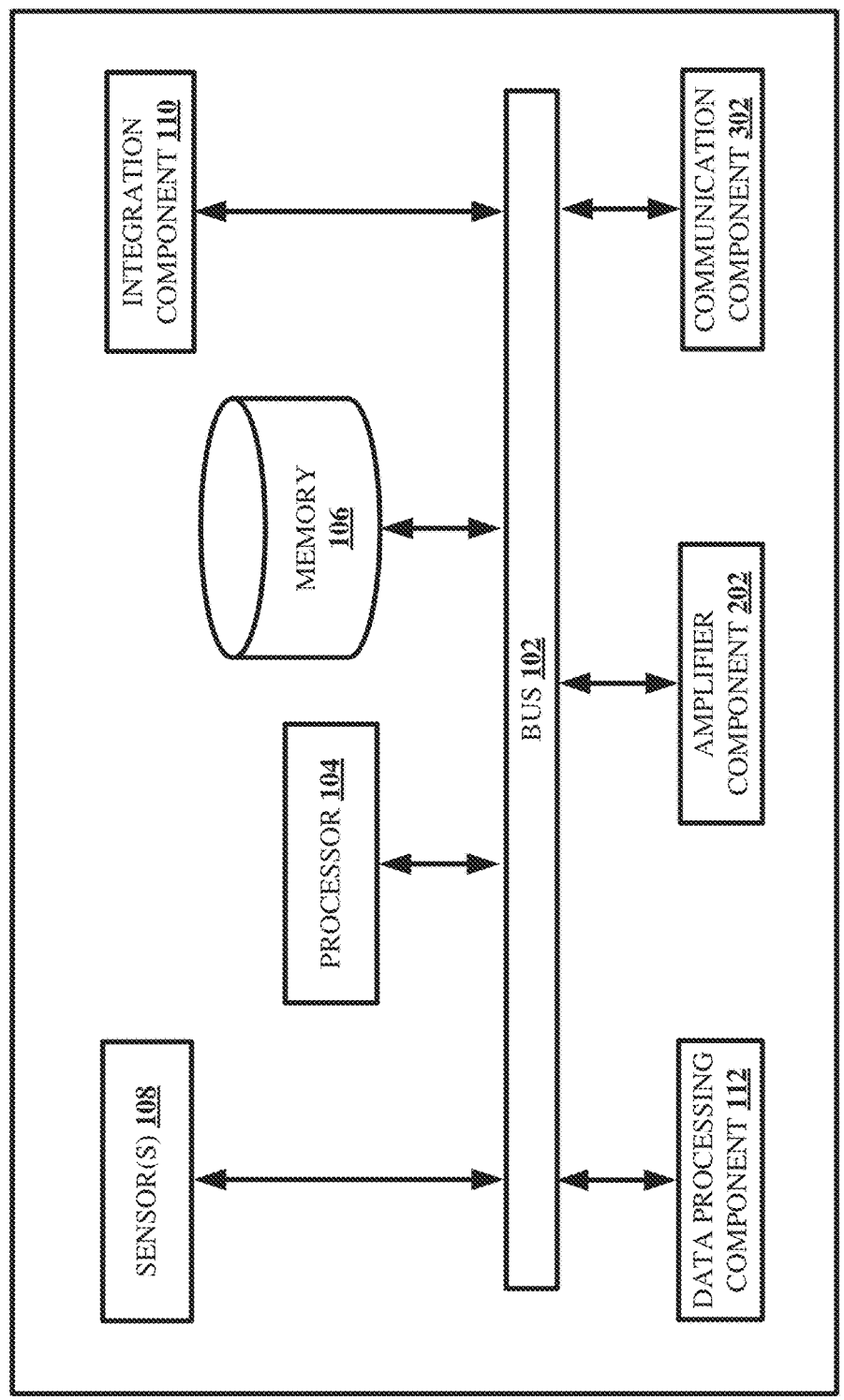
FIG. 3 illustrates a block diagram of an example, non-limiting system facilitating wearable multiplatform sensing including a communication component in accordance with one or more embodiments described herein.

FIG. 3 illustrates a block diagram of an example, non-limiting system facilitating wearable multiplatform sensing including a communication component 302 in accordance with one or more embodiments described herein. Repetitive description of like elements employed in other embodiments described herein is omitted for sake of brevity. The communication component 302 can transmit and receive digital signals from the one or more devices. The communication component 302 can comprise a controller or microcontroller, Bluetooth® or near field communication transmitter receiver (NFC TXRX) and one or more antennas. The microcontroller can receive digital signals from the amplifier component 202 and facilitate communication with a receiver using Bluetooth® or NFC TXRX. The antennas can be used to transmit the digital signals. An antenna can be configured for near field communication, e.g., less than 10 centimeter (cm), and another antenna can be configured for far field communication, e.g., greater than 15 cm. The antennas can be configured to transmit and receive digital signal.

Figure 4:
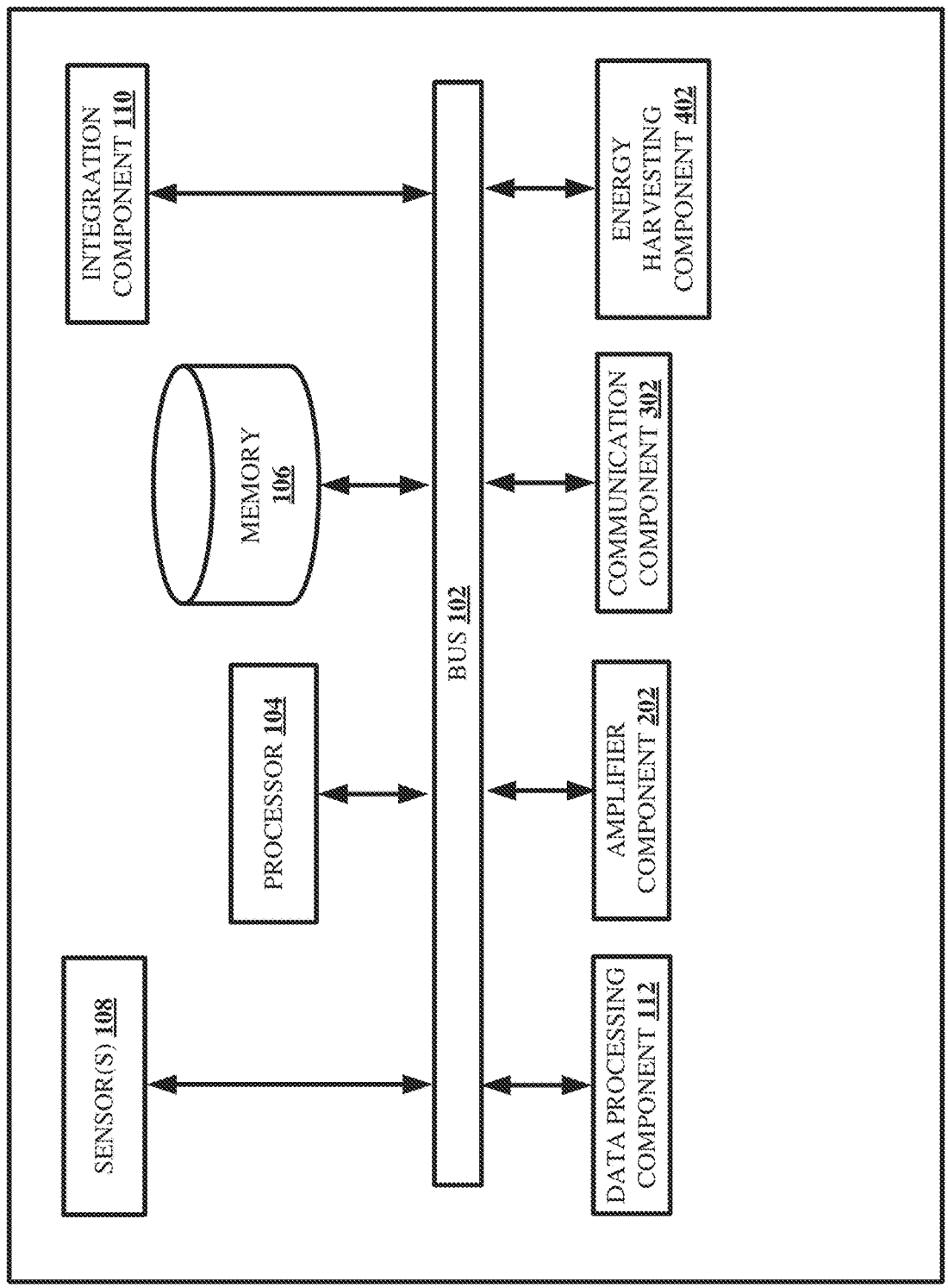
FIG. 4 illustrates a block diagram of an example, non-limiting system facilitating wearable multiplatform sensing including an energy harvesting component in accordance with one or more embodiments described herein.

FIG. 4 illustrates a block diagram of an example, non-limiting system facilitating wearable multiplatform sensing including an energy harvesting component 402 in accordance with one or more embodiments described herein.

Repetitive description of like elements employed in other embodiments described herein is omitted for sake of brevity. The energy harvesting component 402 can provide power to the system. The energy harvesting component 402 can employ solar cells, heat from the body of the entity, a capacitor or a battery. For example, the energy harvesting component 402 can harvest energy from solar cells or body heat to provide additional power to the microsystem (e.g., device) along with a battery. In addition, the sensors 108 can be powered on or off (e.g., powered on for use and powered off if not being used) for energy efficiency. Energy can come from internal and external energy sources including, but not limited to, batteries, capacitors, super capacitors, NFC power transfer or other energy transfer methods, photovoltaic (PV) or other energy scavenging methods, and one time use or rechargeable battery or flexible battery.

Figure 5:
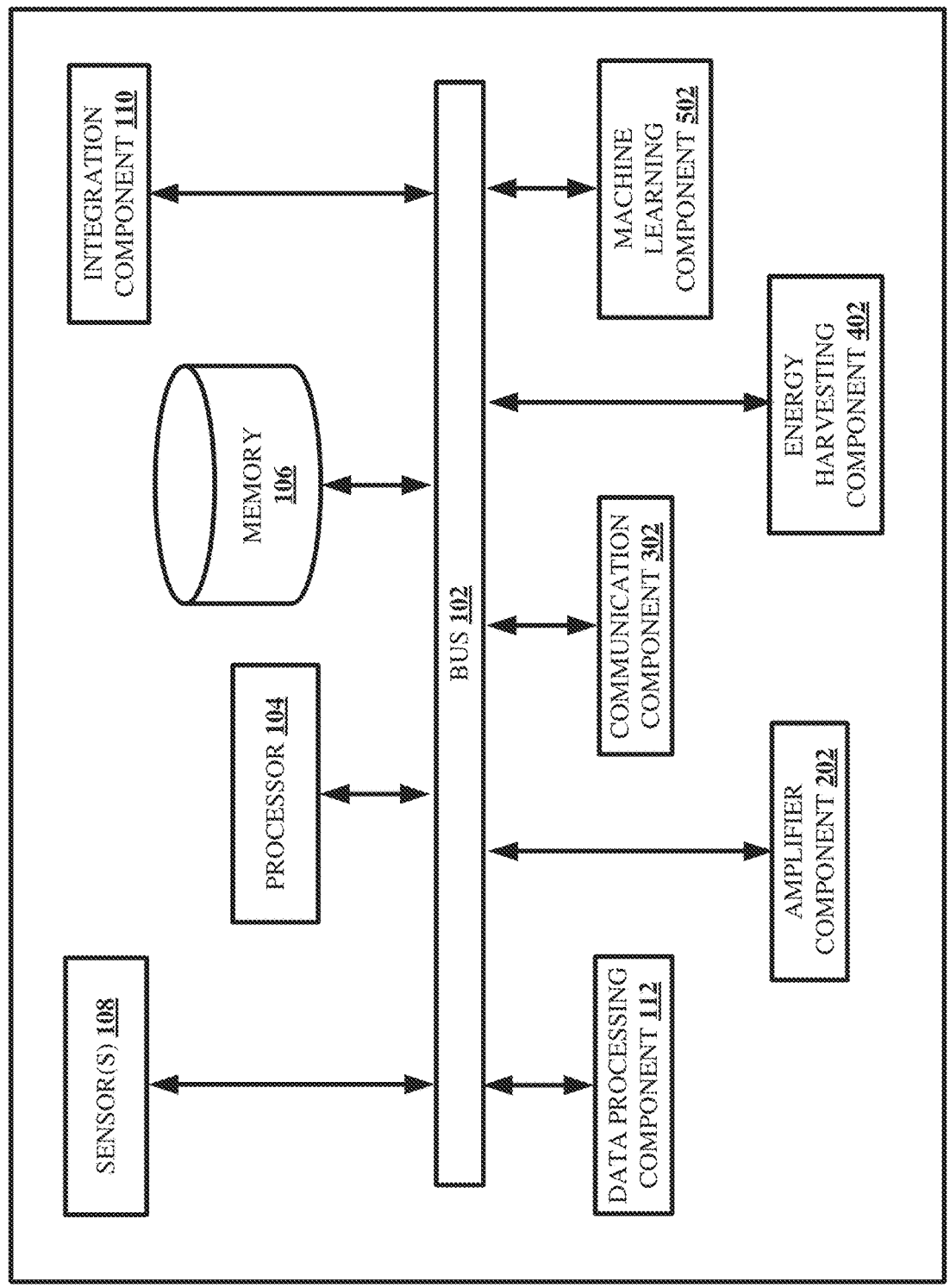
FIG. 5 illustrates a block diagram of an example, non-limiting system facilitating wearable multiplatform sensing including a machine learning component in accordance with one or more embodiments described herein.

FIG. 5 illustrates a block diagram of an example, non-limiting system facilitating wearable multiplatform sensing including a machine learning component 502 in accordance with one or more embodiments described herein. Repetitive description of like elements employed in other embodiments described herein is omitted for sake of brevity. The machine learning component 502 can learn the physiological data from the one or more sensors based on placement location of the one or more sensors 108 for insights on the placement location to optimize sensitivity of the sensors. For example, the machine learning component 502 can analyze the physiological data of users with fingernail sensors and provide insights on placement of the fingernail sensors on the nail bed. The machine learning component 502 can analyze that fingernail sensors located in a region between a third and a half of a fingernail length from the fingertip can be an ideal region for measuring pressure on the fingers. The machine learning component 502 can analyze that fingernail sensors adjacent to the proximal nail fold or in the lunula region can be an ideal region for finger joint bending sensitivity.

Smart multiplexing can enable data streams between the sensors 108, sensor systems (e.g., system 100, devices, etc.) and reader/base station or cloud (not shown). The base station can read information such as physiological data and share the information between base stations, reader or the cloud to be shared between one or more system 100 or devices. The base station can be placed in the home, at work, in an automobile, in a robot or another location of preference. Access to the base station can be given to an authorized individual such as, but not limited to, a caregiver, doctor or family member.

Figure 6:
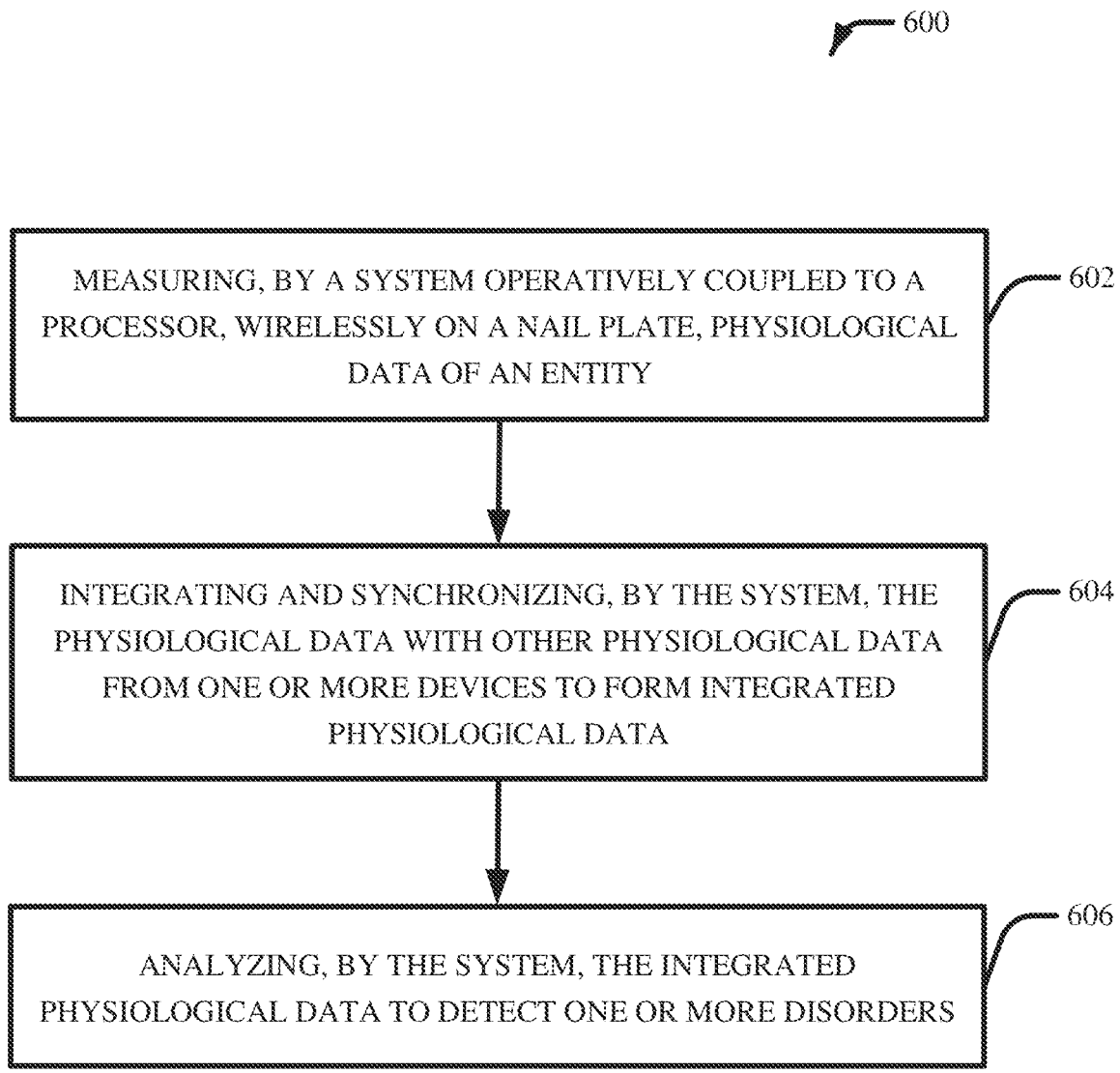
FIG. 6 illustrates a flow diagram of an example, non-limiting computer-implemented method facilitating wearable multiplatform sensing in accordance with one or more embodiments described herein.

FIG. 6 illustrates a flow diagram of an example, non-limiting computer-implemented method 600 facilitating wearable multiplatform sensing in accordance with one or more embodiments described herein. Repetitive description of like elements employed in other embodiments described herein is omitted for sake of brevity. At 602, the computer-implemented method 600 can comprise measuring (e.g., via the sensors 108), by a system operatively coupled to a processor, wirelessly on a nail plate, physiological data of an entity. At 604, the computer-implemented method can comprise integrating and synchronizing (e.g., via the integration component 110), by the system, the physiological data with other physiological data from one or more devices to form integrated physiological data. At 606, the computer-implemented method can comprise analyzing (e.g., data processing component 112), by the system, the integrated physiological data to detect one or more disorders.

Figure 7:
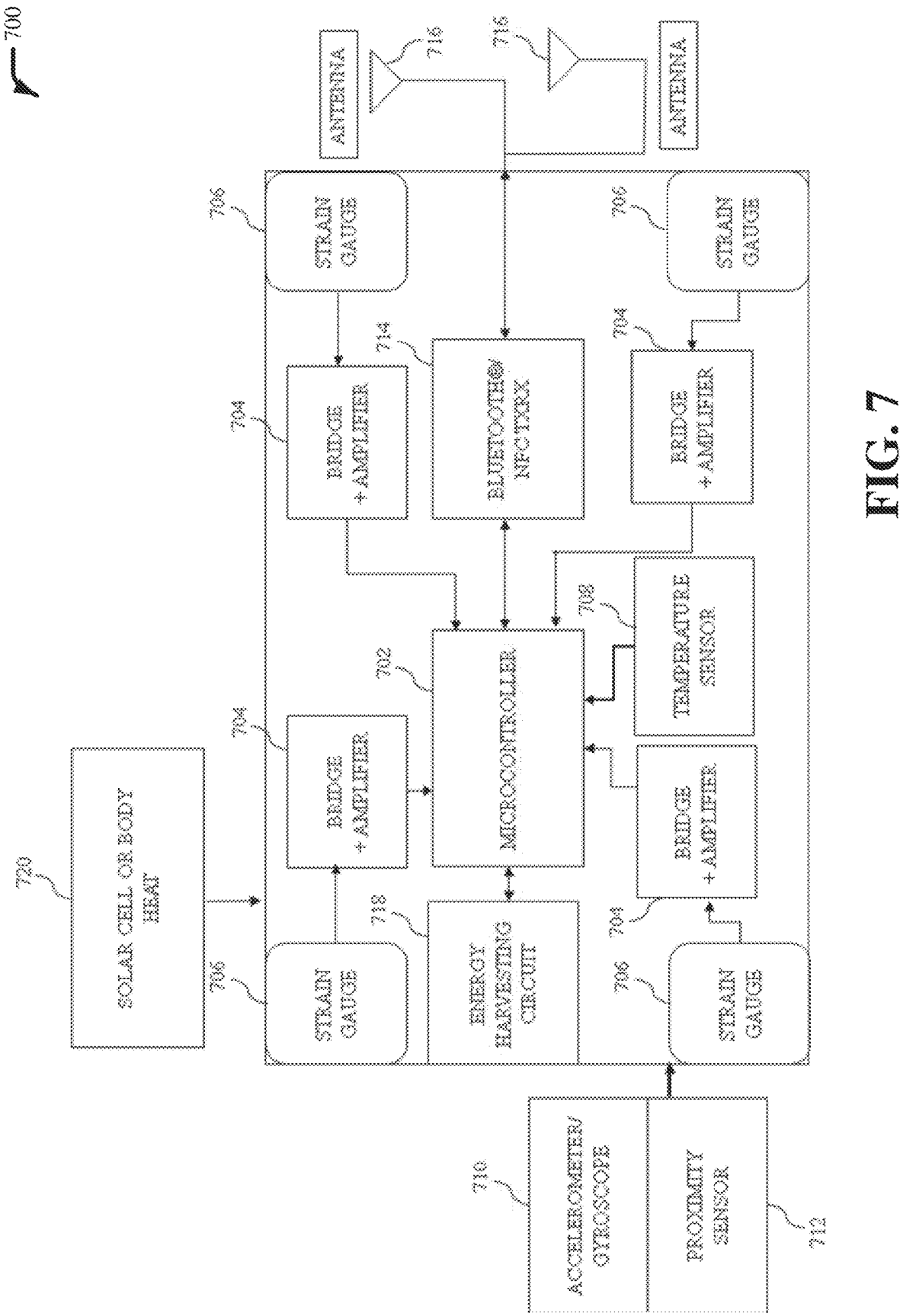
FIG. 7 illustrates a block diagram of an example, non-limiting sensor system facilitating wearable multiplatform sensing in accordance with one or more embodiments described herein.

FIG. 7 illustrates a block diagram of an example, non-limiting sensor system 700 facilitating wearable multiplatform sensing in accordance with one or more embodiments described herein. Repetitive description of like elements employed in other embodiments described herein is omitted for sake of brevity. In this example, the sensor system 700 can be a fingernail sensor system small enough to be attached to the fingernails. However, it is appreciated that the sensor system 700 can be placed in different locations on a user. The sensor system 700 can be a modular form so that components in the sensor system 700 can be modified or replaced to measure a broad range of data depending on placement location of the sensor system 700. For example, architecture options can depend on local data storage, time or duration of use between data collection and data transfer and charge or recharge of device.

The sensor system 700 can be an SoC or SoP. The sensor system 700 can comprise a microcontroller 702, four bridge+amplifiers 704 (e.g., bridge circuit and amplifier circuit), four strain gauges 706, temperature sensor 708, accelerometer/gyroscope 710, proximity sensor 712, Bluetooth®/NFC TXRX 714, two antennas 716, energy harvesting circuit 718 and solar cell or body heat 720. The dimension of the sensor system 700 can be as small as 0.6 millimeter (mm) by 0.6 mm without the two antenna 716.

The strain gauges 706 can measure low and high frequency vibrations, pressure change (e.g., force) and so forth. Depending the placement of the sensor system 700, the strain gauges 706 can also be modified to measure weight. For example, the sensor system 700 can be placed on an injured foot of an animal to track use of the injured limb and monitor the healing process. Other sensors can include, but not limited to temperature sensor 708, accelerometer/gyroscope 710 and proximity sensor 712. The temperature sensor 708 can measure temperature changes. The accelerometer/gyroscope 710 can measure acceleration and orientation. The proximity sensor 712 can detect presence of nearby objects.

The microcontroller 702 can receive digital signals from the bridge+amplifier 704 and facilitate communication with a receiver (e.g., receiver of a base station, another device, cloud, etc.) using Bluetooth®/NFC TXRX 714. The two antennas 716 can be used to transmit the digital signals. One of the two antennas 716 can be configured for near field communication, e.g., less than 10 centimeter (cm), and the other antenna 716 can be configured for far field communication, e.g., greater than 15 cm. The antennas 716 can be configured to transmit and receive the digital signals.

Figure 8:
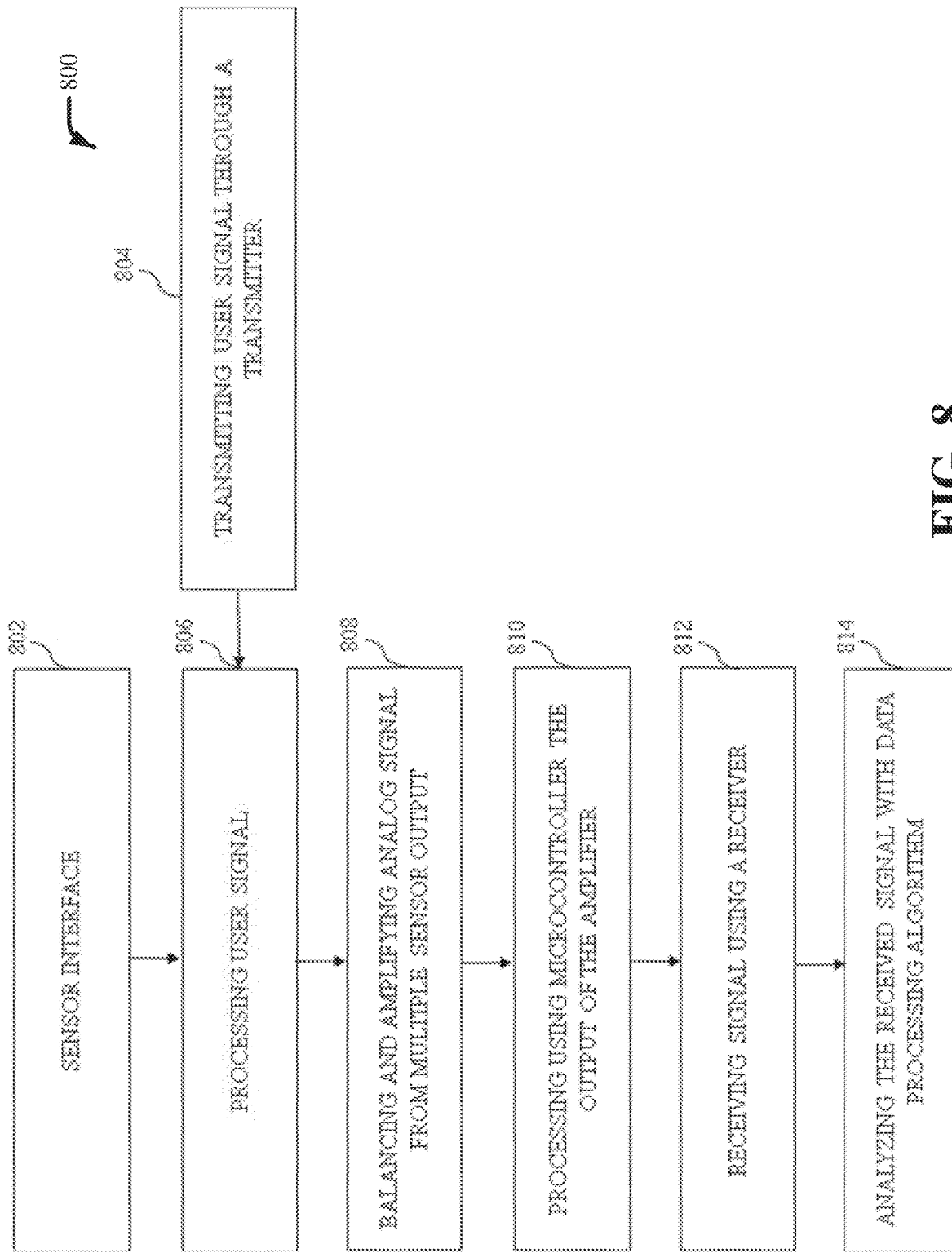
FIG. 8 illustrates a flow diagram of an example, non-limiting computer-implemented method facilitating wearable multiplatform sensing in accordance with one or more embodiments described herein.

The energy harvesting circuit 718 can be a power management unit that can use a combination of solar cells or body heat 720 or NFC, supercapacitor and batter to power the sensor system 700. The energy harvesting circuit 718 can provide additional power to the sensor system 700 from solar cells or body heat 720 along with a battery. Near field communication can provide additional power to the sensor system 700 by using an electromagnetic field. The batteries can be a one-time use or rechargeable battery or flexible battery FIG. 8 illustrates a flow diagram of an example, non-limiting computer-implemented method 800 facilitating wearable multiplatform sensing in accordance with one or more embodiments described herein. Repetitive description of like elements employed in other embodiments described herein is omitted for sake of brevity. At 802, the computer-implemented method 800 can comprise interfacing (e.g., via the sensors 108) the sensor. At 804, the computer-implemented method 800 can comprise transmitting (e.g., via the communication component 302 from other system 100) user signal through a transmitter. At 806, the computer-implemented method 800 can comprise processing (e.g., via the processor 104) user signal. At 808, the computer-implemented method 800 can comprise balancing and amplifying (e.g., via the amplifier component 202) analog signal from multiple sensor output. At 810, the computer-implemented method 800 can comprise processing (e.g., via the communication component 302) using microcontroller the output of the amplifier. At 812, the computer-implemented method 800 can comprise receiving (e.g., via the communication component 302) signal using a receiver. At 814, the computer-implemented method 814 can comprise analyzing (e.g., data processing component 112) the received signal with data processing algorithm.

Figure 9:
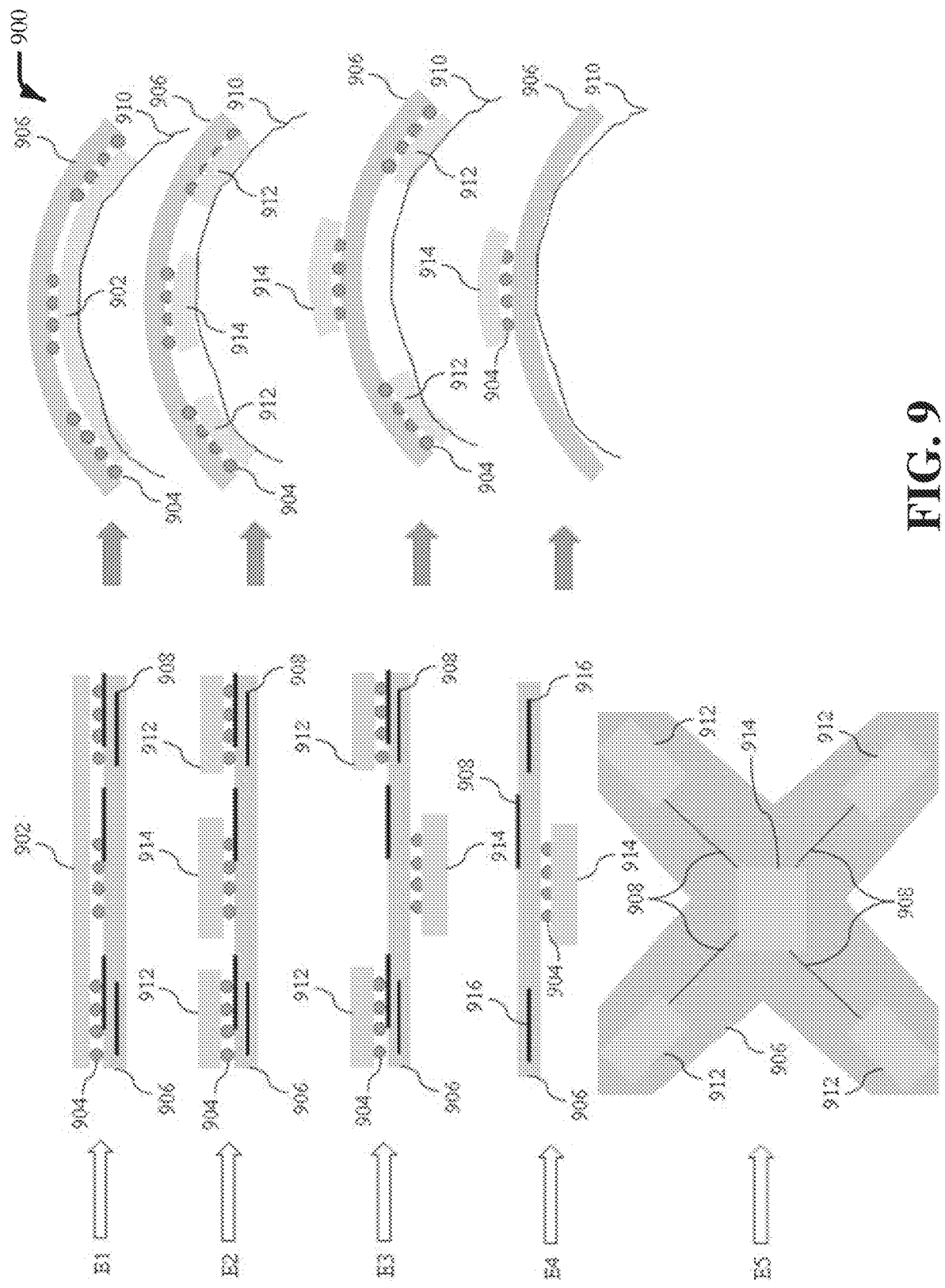
FIG. 9 illustrates a block diagram of an example, non-limiting system-on-chip (SoC) structure facilitating wearable multiplatform sensing in accordance with one or more embodiments described herein.

FIG. 9 illustrates a block diagram of an example, non-limiting system-on-chip (SoC) structure 900 facilitating wearable multiplatform sensing in accordance with one or more embodiments described herein. Repetitive description of like elements employed in other embodiments described herein is omitted for sake of brevity. Example E1 illustrates strain gauge and microcontroller 902 connected to flexible substrate 906 by the controlled collapse chip connection (C4) solder micro-bump. Wiring 908 can be embedded within flexible substrate 906. The strain gauge and microcontroller 902 can comprise a silicon substrate that can extend a length of the flexible substrate 906. During CMOS or sensor fabrication process, the silicon substrate can be 500 to 800 μm thick. Grinding or polishing of the silicon substrate to less than 100 μm thick can facilitate bending of the silicon substrate. As illustrate in FIG. 9, the strain gauge and microcontroller 902 can bend with the flexible substrate 906 to form along the nail bed 910. The strain gauge and microcontroller 902 side (e.g., side comprising strain gauge) can be attached to the nail bed 910 by using an adhesive.

In example E1 to E5, a barrier packaging or hermetic sealing such as, but not limited to, a polymer or a thin metal plate (not shown) can surround the SoC structure 900 for prolonged use, life and reliability. As in Example E1, the strain gauge 912 and microcontroller 914 in examples E2 to E5 can also bend or form along the nail bed 910. The strain gauge 912 and microcontroller 914 can comprise a silicon substrate that can be grinded or polished to less than 100 μm thick to facilitate bending or forming along the nail bed 910.

Example E2 can comprise two strain gauges 912 and a microcontroller 914 disposed on the same side of the flexible silicon substrate 906. The microcontroller 914 can be disposed between the two strain gauges 912. Wiring 908 can be embedded within flexible substrate 906. The two strain gauges 912 and microcontroller 914 can be connected to the flexible substrate 906 by the C4 solder micro-bump 904. The strain gauge 912 side can be attached to the nail bed 910 using an adhesive. The strain gauges 912 and microcontroller 914 can stay connected to the flexible substrate 906 that can form along the nail bed 910.

Example E3 can comprise two strain gauges 912 disposed on the same side of the flexible substrate 906 at opposite ends and a microcontroller 914 disposed between the strain gauge 912 on the opposite side of the flexible substrate 906. Wiring 908 can be embedded within flexible substrate 906. The two strain gauges 912 and microcontroller 914 can be connected to the flexible substrate 906 by the C4 solder micro-bump 904. The strain gauge 912 side can be attached to the nail bed 910 using an adhesive. The strain gauges 912 and microcontroller 914 can stay connected to the flexible substrate 906 that can form along the nail bed 910.

Example E4 can comprise two embedded strain gauges 916 at opposite ends of the flexible substrate 906. The two embedded strain gauges 916 can be embedded in the flexible substrate 906. The microcontroller 914 can be disposed between the two embedded strain gauges 916 and connected to a side of the flexible substrate 906. The microcontroller 914 can be connected to the flexible substrate 906 by the C4 solder micro-bump 904. The flexible substrate 906 and microcontroller 914 can form along the nail bed 910. The side of the flexible substrate 906 not connected to the microcontroller 914, which can be closer to the embedded strain gauge 916, can be attached to the nail bed 910 using an adhesive.

Example E1 to E4 illustrates a linear alignment of the strain gauge and microcontroller 902, strain gauge 912, microcontroller 914 and embedded strain gauge 916. Example E5 illustrates a flexible substrate 906, wiring 908, four strain gauges 912 (or embedded strain gauges 916) and microcontroller 914 in an X shape. The flexible substrate 906 can be an X shape. The microcontroller 914 can be placed in the center of the X shape and the four strain gauges 912 (or embedded strain gauges 916) can be placed at the corner ends of the X shape. Wiring 908 can electrically connect the four strain gauges 912 (or embedded strain gauges 916) to the microcontroller 914. It is appreciated that example E1 to E5 are illustrative of the possible arrangements and combinations of strain gauge and microcontroller that are not exhaustive of the possible arrangements.

Figure 10:
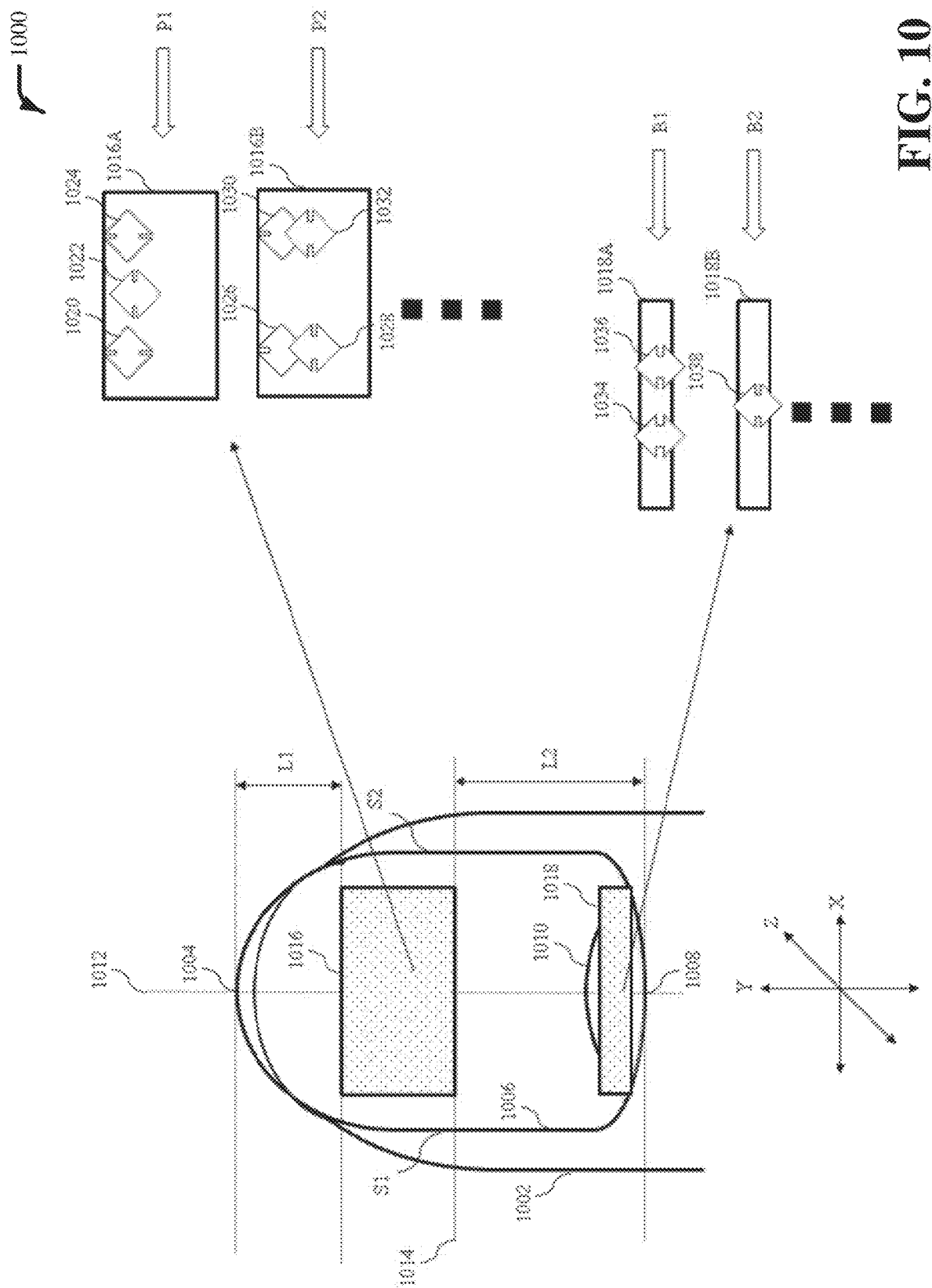
FIG. 10 illustrates a block diagram of an example, non-limiting fingernail strain sensor positions facilitating wearable multiplatform sensing in accordance with one or more embodiments described herein.

FIG. 10 illustrates a block diagram of an example, non-limiting fingernail strain sensor positions 1000 facilitating wearable multiplatform sensing in accordance with one or more embodiments described herein. Repetitive description of like elements employed in other embodiments described herein is omitted for sake of brevity. FIG. 10 illustrates finger 1002 comprising fingertip 1004, nail bed 1006, proximal nail fold 1008 and lunula 1010. Longitudinal line 1012 can extend lengthwise along the nail bed 1006 through the proximal nail fold 1008 and fingertip 1004. The transverse line 1014 can extend crosswise across the nail bed 1006. The transverse line 1014 can be orthogonal to longitudinal line 1012.

Sensors devices (e.g., devices comprising sensor 108) can comprise strain gauge sensors (e.g., strain sensors) with differing sense directions that detect strains in a fingernail or toenail based on pressure on a tip of a finger or toe. The region 1016 can be an ideal region for measuring pressure on finger 1002. Region 1016 can be located in a region between one third of the length of the fingernail from the fingertip 1004 (length L1) and one half of the length of the fingernail (length L2). Example sensor position P1 and P2 can illustrate position and orientation of strain sensors for region 1016. For example, exemplary sensor position P1 illustrates region 1016A comprising strain sensor 1020, strain sensor 1022 and strain sensor 1024 in a linear arrangement. The strain sensor 1022 can be disposed between strain sensor 1020 and strain sensor 1024. The strain sensor 1020 and strain sensor 1024 can measure pressure in the X direction (e.g., along transverse direction 1014), and strain sensor 1022 can measure pressure in the Y direction (e.g., along longitudinal direction 1012). It is appreciated that depending on the placement of the strain sensors, strain sensors can also measure pressure in the Z direction (e.g., weight or pressure points).

Example sensor position P2 illustrates region 1016B comprising strain sensor 1026 overlapped by strain sensor 1028 and strain sensor 1030 overlapped by strain sensor 1032. The sets of overlapped sensors can be disposed alongside one another paralleling in the Y direction. Strain sensor 1026 can measure pressure in X direction, strain sensor 1028 can measure pressure in the Y direction, strain sensor 1030 can measure pressure in the X direction and strain sensor 1032 can measure pressure in the Y direction.

Region 1018 can be an ideal region for finger joint bending sensitivity. Region 1018 (e.g., lunula region) can be at the lunula 1010 and close to the proximal nail fold 1008. Example bending sensitivity position B1 and B2 can illustrate position and orientation of strain sensors for region 1018. For example, example bending sensitivity position B1 illustrates region 1018A comprising strain sensor 1034 and strain sensor 1036 disposed alongside one another. The strain sensor 1034 and strain sensor 1036 can measure pressure in the Y direction.

Example bending sensitivity position B2 illustrates region 1018B comprising strain sensor 1038 in the center of the region 1018B. The strain sensor 1038 can measure pressure in the Y direction. Illustrated in FIG. 10 are possible region, position and orientation of strain sensors (e.g., sensors 108). The machine learning component 502 can learn the physiological data from the strain sensors (e.g., sensors 108) based on placement location of the strain sensors (e.g., sensors 108) for insights on the placement location. An array of sensors devices (e.g., devices comprising sensor 108) can be valuable because it can provide the system (e.g., system 100 and the like) additional information to resolve disparate motions and loading of the finger. Sensor devices at the base (e.g., lunula 1010 or region 1018) of the nail can be used to observe axial compression (e.g., pressure in the Y direction or longitudinal direction 1012) when the distal interphalangeal (DIP) joint is allowed to bend as the fingertip is pressed. Axial compression may not be present when the DIP joint is held rigid because the suspensory ligaments (e.g., collateral ligaments) can have compression or tension forces. Similarly, transverse (e.g., in the X direction or transverse direction 1014) sliding motions of the finger can roll soft tissue to the side, compressing the nail in the transverse direction 1014 on one side (e.g., side S1 or side S2) while creating tension on the other side. A rolling motion of the fingertip can also have a smaller tensional element. Other motions can induce other distributions of compression and tension in other directions on different parts of the nail. For simple fingertip pressure such as downward pressing, the largest strains can be on points along the finger axis (e.g., longitudinal direction 1012) between a half and a third of the way back from the fingertip. By placing the sensor devices at multiple locations on a finger, the data collected can be used to learn how a finger is being held and whether it is pressing. The placement of sensor devices on multiple locations of a finger and on multiple fingers can be used to learn the motion of the hand.

It is appreciated that the ideal region for placing sensor device on fingers can depend on the type of sensors. For example, the ideal region for PPG sensors, optical device or photodetector can be on the sides of the fingernail and/or toenail for reflective sensing or transmission sensing. For example, a fingernail or toenail can have two optical devices (not shown) attached. One optical device can be attached to a first side S1 and the other optical device can be attached to a second side S2. Example optical devices can include, but not limited to, a light source (e.g., LED) attached to side S1 and a photodetector (e.g., photodiode) attached the other side S2 of the fingernail or toenail. It is appreciated that the light source can be attached to side S2 and the photodetector can be attached to side S1. It is also appreciated that the light source and photodetector can both be attached to the same side, side S1 or side S2. The LED can transmit different light wavelengths through the skin, and a partial discharge detector (not shown) can measure the non-absorbed light that is either transmitted through (e.g., transmission mode) or reflected by (e.g., reflectance or reflective mode) the bone, veins, and other tissues below the skin. The non-absorbed light received at the detector can be used to measure the actual difference in the absorption spectra of oxygenated hemoglobin ($HbO_2$) and deoxygenated hemoglobin (Hb). This can be used to measure the blood oxygen level or saturation of peripheral oxygen ($SPO_2$).

Figure 11:
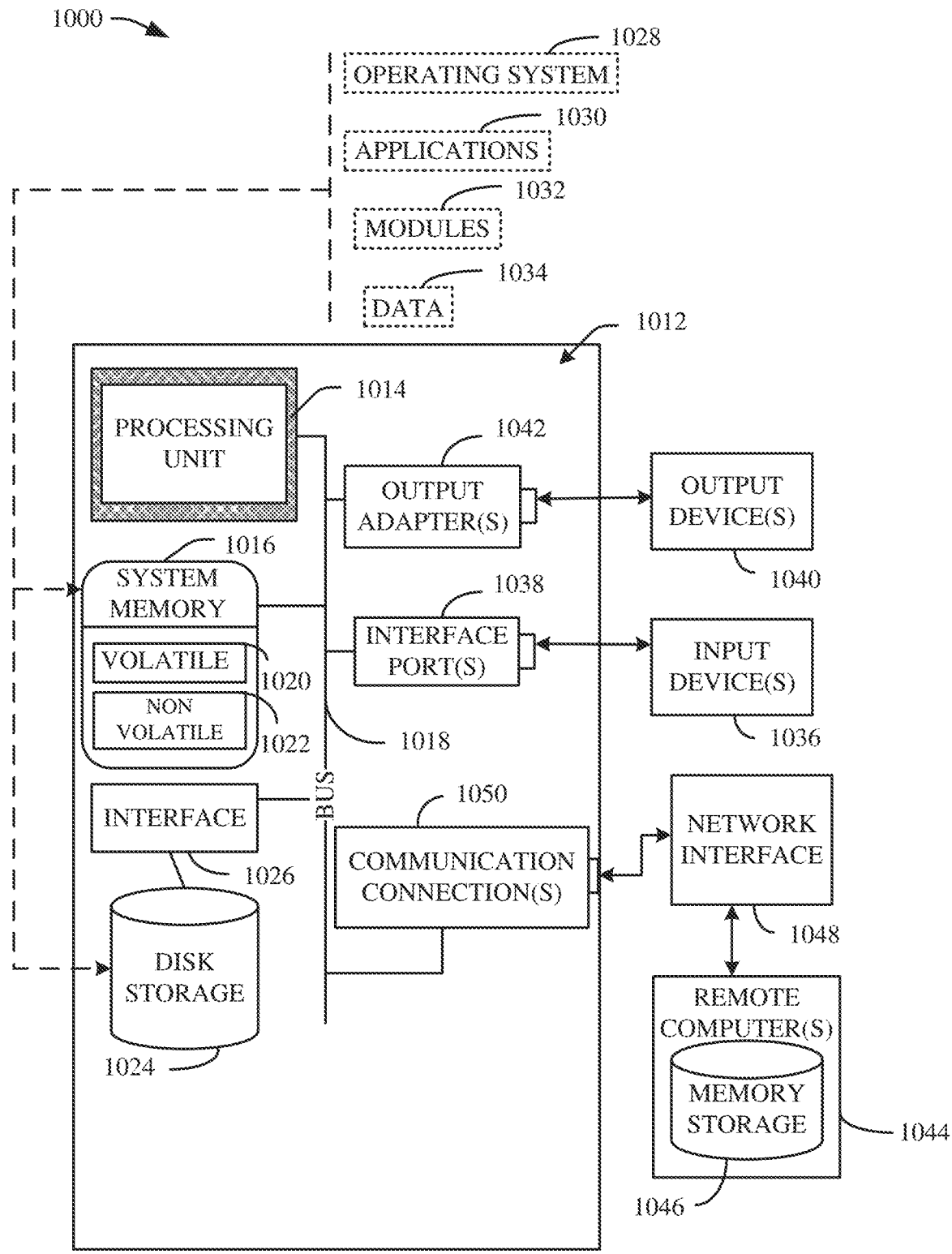
FIG. 11 illustrates a block diagram of an example, non-limiting operating environment in which one or more embodiments described herein can be facilitated.

In order to provide a context for the various aspects of the disclosed subject matter, FIG. 11 as well as the following discussion are intended to provide a general description of a suitable environment in which the various aspects of the disclosed subject matter can be implemented. FIG. 11 illustrates a block diagram of an example, non-limiting operating environment in which one or more embodiments described herein can be facilitated. Repetitive description of like elements employed in other embodiments described herein is omitted for sake of brevity.

With reference to FIG. 11, a suitable operating environment 1100 for implementing various aspects of this disclosure can also include a computer 1112. The computer 1112 can also include a processing unit 1114, a system memory 1116, and a system bus 1118. The system bus 1118 couples system components including, but not limited to, the system memory 1116 to the processing unit 1114. The processing unit 1114 can be any of various available processors. Dual microprocessors and other multiprocessor architectures also can be employed as the processing unit 1114. The system bus 1118 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 1116 can also include volatile memory 1120 and nonvolatile memory 1122. The basic input/output system (BIOS), containing the basic routines to transfer information between elements within the computer 1112, such as during start-up, is stored in nonvolatile memory 1122. Computer 1112 can also include removable/non-removable, volatile/non-volatile computer storage media. FIG. 11 illustrates, for example, a disk storage 1124. Disk storage 1124 can also include, but is not limited to, devices like a magnetic disk drive, floppy disk drive, tape drive, Jaz drive, Zip drive, LS-100 drive, flash memory card, or memory stick. The disk storage 1124 also can include storage media separately or in combination with other storage media. To facilitate connection of the disk storage 1124 to the system bus 1118, a removable or non-removable interface is typically used, such as interface 1126. FIG. 11 also depicts software that acts as an intermediary between users and the basic computer resources described in the suitable operating environment 1100. Such software can also include, for example, an operating system 1128. Operating system 1128, which can be stored on disk storage 1124, acts to control and allocate resources of the computer 1112.

System applications 1130 take advantage of the management of resources by operating system 1128 through program modules 1132 and program data 1134, e.g., stored either in system memory 1116 or on disk storage 1124. It is to be appreciated that this disclosure can be implemented with various operating systems or combinations of operating systems. A user enters commands or information into the computer 1112 through input device(s) 1136. Input devices 1136 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1114 through the system bus 1118 via interface port(s) 1138. Interface port(s) 1138 include, for example, a serial port, a parallel port, a game port, and a universal serial bus (USB). Output device(s) 1140 use some of the same type of ports as input device(s) 1136. Thus, for example, a USB port can be used to provide input to computer 1112, and to output information from computer 1112 to an output device 1140. Output adapter 1142 is provided to illustrate that there are some output devices 1140 like monitors, speakers, and printers, among other output devices 1140, which require special adapters. The output adapters 1142 include, by way of illustration and not limitation, video and sound cards that provide a means of connection between the output device 1140 and the system bus 1118. It should be noted that other devices and/or systems of devices provide both input and output capabilities such as remote computer(s) 1144.

Computer 1112 can operate in a networked environment using logical connections to one or more remote computers, such as remote computer(s) 1144. The remote computer(s) 1144 can be a computer, a server, a router, a network PC, a workstation, a microprocessor based appliance, a peer device or other common network node and the like, and typically can also include many or all of the elements described relative to computer 1112. For purposes of brevity, only a memory storage device 1146 is illustrated with remote computer(s) 1144. Remote computer(s) 1144 is logically connected to computer 1112 through a network interface 1148 and then physically connected via communication connection 1150. Network interface 1148 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1150 refers to the hardware/software employed to connect the network interface 1148 to the system bus 1118. While communication connection 1150 is shown for illustrative clarity inside computer 1112, it can also be external to computer 1112. The hardware/software for connection to the network interface 1148 can also include, for exemplary purposes only, internal and external technologies such as, modems including regular telephone grade modems, cable modems and DSL modems, ISDN adapters, and Ethernet cards.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 12:
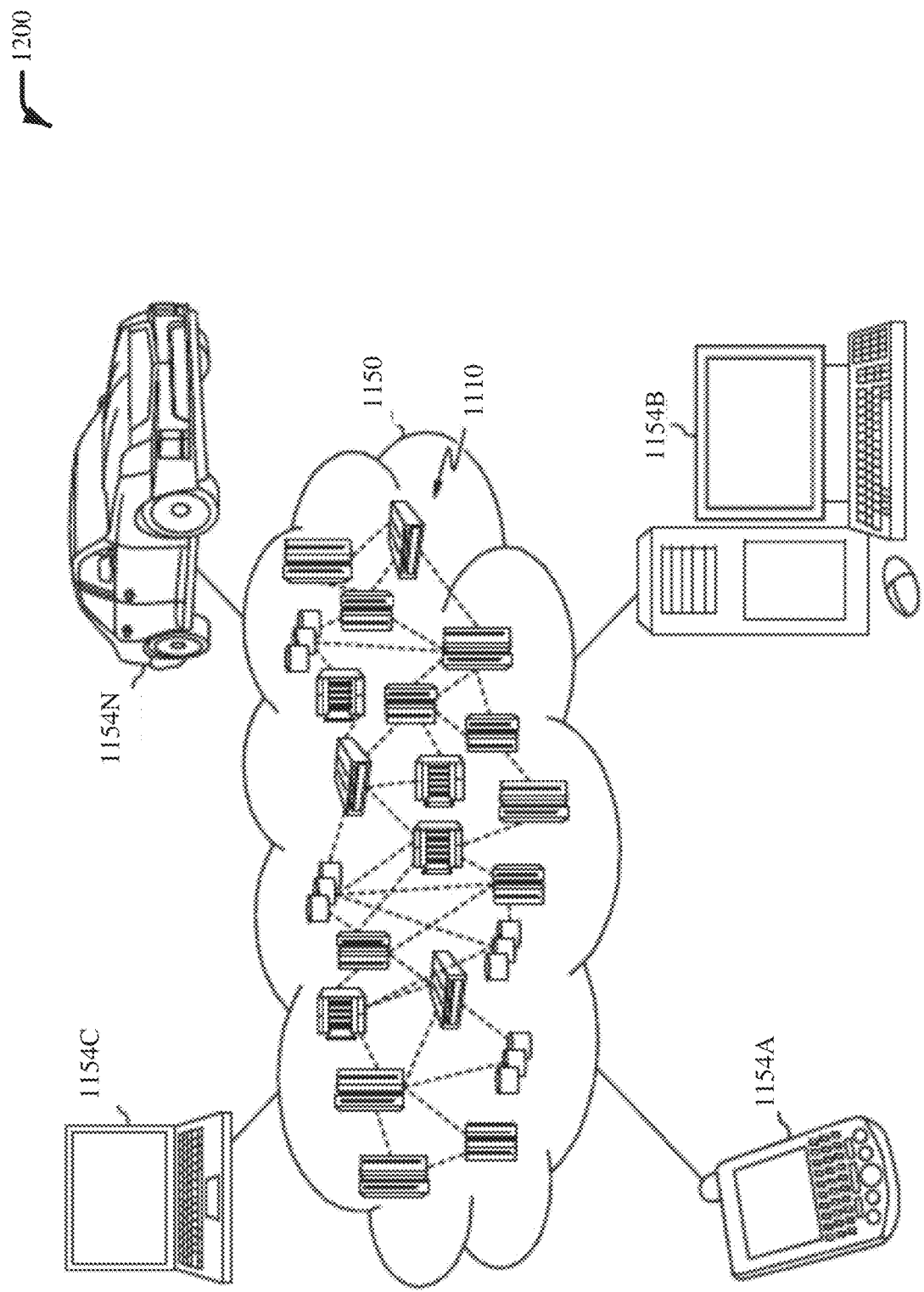
FIG. 12 illustrates a block diagram of an example, non-limiting cloud computing environment in accordance with one or more embodiments described herein.

Referring now to FIG. 12, an illustrative cloud computing environment 1250 is depicted. As shown, cloud computing environment 1250 includes one or more cloud computing nodes 1210 with which local computing devices used by cloud consumers, such as, for example, personal digital assistant (PDA) or cellular telephone 1254A, desktop computer 1254B, laptop computer 1254C, and/or automobile computer system 1254N may communicate. Nodes 1210 may communicate with one another. They may be grouped (not shown) physically or virtually, in one or more networks, such as Private, Community, Public, or Hybrid clouds as described hereinabove, or a combination thereof. This allows cloud computing environment 1250 to offer infrastructure, platforms and/or software as services for which a cloud consumer does not need to maintain resources on a local computing device. It is understood that the types of computing devices 1254A-N shown in FIG. 12 are intended to be illustrative only and that computing nodes 1210 and cloud computing environment 1250 can communicate with any type of computerized device over any type of network and/or network addressable connection (e.g., using a web browser).

Figure 13:
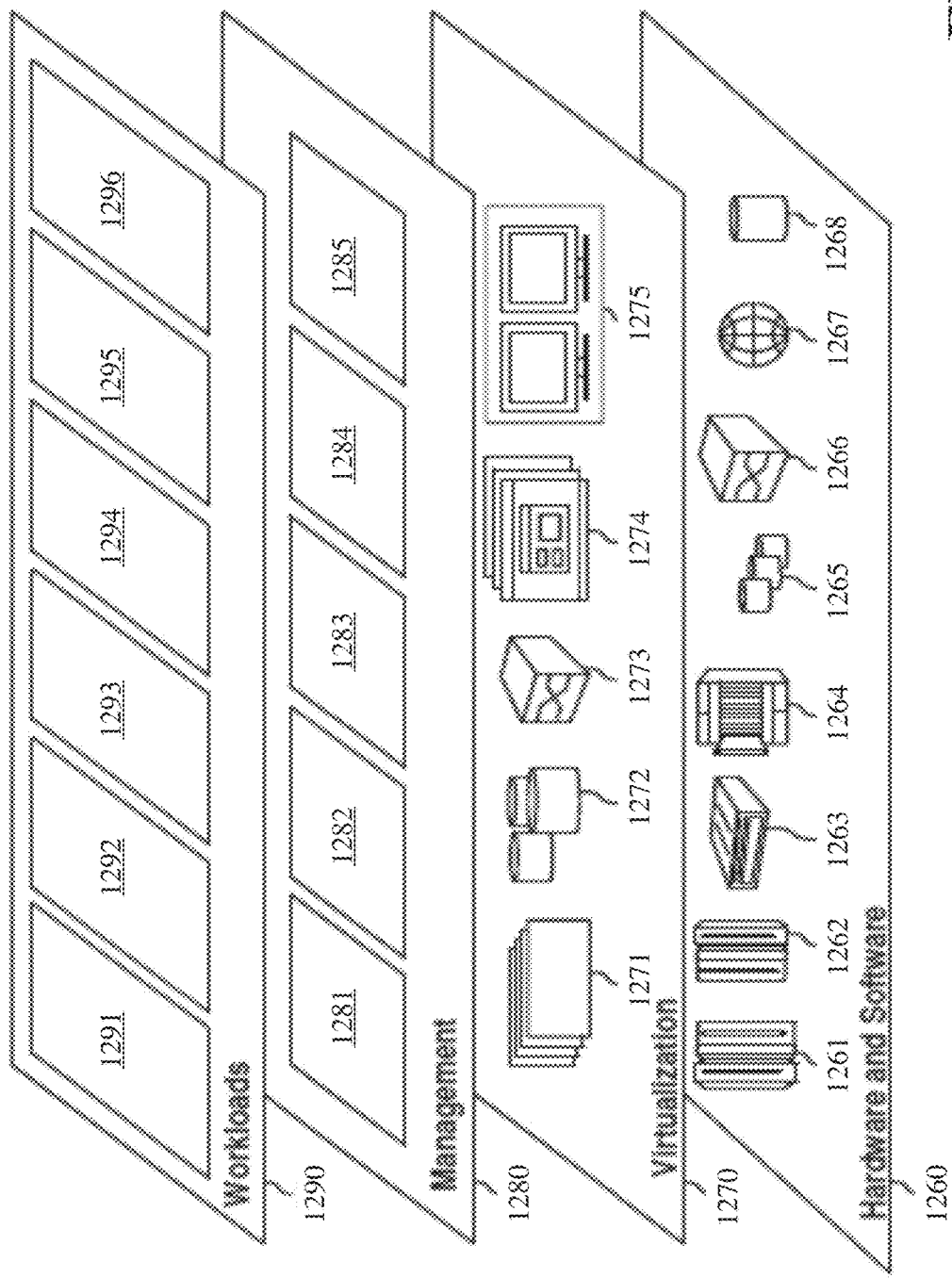
FIG. 13 illustrates a block diagram of example, non-limiting abstraction model layers in accordance with one or more embodiments described herein.

Referring now to FIG. 13, a set of functional abstraction layers provided by cloud computing environment 1250 (FIG. 12) is shown. It should be understood in advance that the components, layers, and functions shown in FIG. 13 are intended to be illustrative only and embodiments of the invention are not limited thereto. As depicted, the following layers and corresponding functions are provided:

Hardware and software layer 1360 includes hardware and software components. Examples of hardware components include: mainframes 1361; RISC (Reduced Instruction Set Computer) architecture based servers 1362; servers 1363; blade servers 1364; storage devices 1365; and networks and networking components 1366. In some embodiments, software components include network application server software 1367 and database software 1368.

Virtualization layer 1370 provides an abstraction layer from which the following examples of virtual entities may be provided: virtual servers 1371; virtual storage 1372; virtual networks 1373, including virtual private networks; virtual applications and operating systems 1374; and virtual clients 1375.

In one example, management layer 1380 may provide the functions described below. Resource provisioning 1381 provides dynamic procurement of computing resources and other resources that are utilized to perform tasks within the cloud computing environment. Metering and Pricing 1382 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1383 provides access to the cloud computing environment for consumers and system administrators. Service level management 1384 provides cloud computing resource allocation and management such that required service levels are met. Service Level Agreement (SLA) planning and fulfillment 1385 provide pre-arrangement for, and procurement of, cloud computing resources for which a future requirement is anticipated in accordance with an SLA.

Workloads layer 1390 provides examples of functionality for which the cloud computing environment may be utilized. Non-limiting examples of workloads and functions which may be provided from this layer include: mapping and navigation 1391; software development and lifecycle management 1392; virtual classroom education delivery 1393; data analytics processing 1394; transaction processing 1395; and mobile desktop 1396.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory; and
   a processor that:
      obtains measurements, using sensors, of vibration of an entity generating vibration data, wherein the vibration data comprises data or signals associated with and generated by the vibration of the entity, wherein at least one of the sensors is adapted to be on a nail plate of the entity;
      integrates and synchronizes the vibration data from a first sensor of the sensors with light data from a light sensor of the sensors,
         wherein the light sensor detects light associated with the nail plate,
         wherein the integration and the synchronization is performed employing artificial intelligence, and
         wherein the integration and the synchronization forms integrated and synchronized physiological data; and
      determines one or more disorders of the entity based on the integrated and synchronized physiological data, wherein the sensors comprise three or more sensors and wherein at least two of the sensors are positioned alongside one another in a first sensor region and wherein a third sensor of the sensors is positioned between at least two sensors in a second sensor region, wherein the first sensor region and the second sensor region are positioned in a linear arrangement relative to one another, and wherein the at least two sensors in the first sensor region and wherein the third sensor in the second sensor region have differing sense directions, wherein the at least two sensors measure pressure along a transverse direction and wherein the third sensor measures pressure along a longitudinal direction.

2. The system of claim 1, wherein the sensors comprise strain gauge sensors that measure respective strains in different directions in the nail plate based on pressure on a tip of the nail plate, wherein the nail plate is part of a fingernail or a toenail.

3. They system of claim 2, wherein the strain gauge sensors are semiconductor strain gauge die having a thickness less than 100 micrometer.

4. The system of claim 2, wherein the strain gauge sensors are located on or embedded in a flexible organic substrate material.

5. The system of claim 4, wherein the strain gauge sensors are attachable on a first side or a second side of the flexible organic substrate material, wherein the first side is opposite the second side and wherein the first side is disposed on a surface.

6. The system of claim 2, wherein two sensors of the three or more sensors are adapted to be positioned on the nail plate of the fingernail or the toenail to sense transverse motions based on positioning the two sensors or rolling motions of a finger or a toe.

7. The system of claim 2, wherein at least one of the sensors are two or more sensors adapted to be positioned in a region between one third and one half of a length of the nail plate in a linear arrangement to sense pressure on a finger associated with nail plate of the entity.

8. The system of claim 2, wherein the three or more sensors are adapted to be positioned in a lunula region to detect motion of a distal interphalangeal (DIP) joint.

9. The system of claim 2, wherein the sensors comprise a photodetector adapted to be attached on a side of the nail plate or on opposite sides of the fingernail or the toenail to detect blood oxygen level.

10. The system of claim 1, wherein the processor also amplifies the vibration data from the sensors.

11. The system of claim 1, wherein the processor also communicates with one or more devices.

12. The system of claim 1, wherein the processor also communicates with an energy harvesting circuit to facilitate harvest of external power for the system.

13. The system of claim 12, wherein the external power comprises at least one of a solar cell, heat from the entity, a capacitor, or a battery.

14. The system of claim 1, wherein the processor also learns an optimal placement location of the sensors based on an examination of the vibration data of entities with fingernail sensors.

15. The system of claim 1, wherein the system is a primary device, and wherein the primary device controls operation of one or more secondary devices.

16. A computer-implemented method, comprising:
sensing, by a system operatively coupled to a processor, using sensors, measurements of vibration of an entity generating vibration data, wherein the sensors comprises three or more sensors and wherein at least two of the three or more sensors are positioned alongside one another in a first sensor region and wherein a third sensor of the three or more sensors is positioned between at least two sensors in a second sensor region, wherein the at least two of the three or more sensors measure pressure along a transverse direction and wherein the third sensor of the three or more sensors measures pressure along a longitudinal direction;
integrating and synchronizing, by the system, employing machine learning, the vibration data with other physiological data detected from a body of the entity from one or more devices to form integrated and synchronized physiological data; and
determining, by the system, employing machine learning, one or more medical disorders of the entity based on the integrated and synchronized physiological data.

17. The computer-implemented method of claim 16, further comprising amplifying, by the system, the vibration data from the sensors.

18. The computer-implemented method of claim 16, further comprising receiving, by the system, digital signals from the one or more devices.

19. The computer-implemented method of claim 16, further comprising receiving, by the system, power, and coordinating the integrated and synchronized physiological data with other sensors or devices in a location at which the entity is located or in a second location remote from the location at which the entity is located.

20. A computer program product for facilitating wearable multiplatform sensing, the computer program product comprising a non-transitory computer readable storage medium having program instructions embodied therewith, the program instructions executable by a processor to cause the processor to:
obtain, by the processor, using sensors, measurements of vibration of an entity generating vibration data, wherein at least one of the sensors are located on a nail plate of a finger of the entity, and wherein the sensors comprises three or more sensors and wherein at least two of the three or more sensors are positioned alongside one another in a first sensor region and wherein a third sensor of the three or more sensors is positioned between at least two sensors in a second sensor region, and wherein the first sensor region and the second sensor region are positioned in a linear arrangement relative to one another, wherein the at least two of the three or more sensors measure pressure along a transverse direction and wherein the third sensor of the three or more sensors measures pressure along a longitudinal direction;
control, by the processor, a light emitting diode to transmit different light wavelengths through the finger of the entity;
determine, by the processor, measured non-absorbed ones of the different light wavelengths reflected by or transmitted through a finger of the entity and received at a detector along with the vibration data;
integrate and synchronize, by the processor, the vibration data with the measured non-absorbed ones of the different light wavelengths to form integrated physiological data; and
determine, by the processor, one or more disorders of the entity based on the integrated physiological data.

* * * * *